United States Patent
Karmali

(10) Patent No.: US 7,750,018 B2
(45) Date of Patent: Jul. 6, 2010

(54) USE OF CARBOXIAMIDOTRIAZOLE (CAI) OROTATE IN MACULAR DEGENERATION

(75) Inventor: Rashida A. Karmali, Brooklyn, NY (US)

(73) Assignee: Tactical Therapeutics, Inc, New York, NY (US)

( * ) Notice: Subject to any disclaimer, the term of this patent is extended or adjusted under 35 U.S.C. 154(b) by 248 days.

(21) Appl. No.: 11/634,422

(22) Filed: Dec. 6, 2006

(65) Prior Publication Data

US 2008/0139592 A1    Jun. 12, 2008

(51) Int. Cl.
*A61K 31/505*    (2006.01)

(52) U.S. Cl. .................. 514/274; 514/210.02; 514/532; 514/54

(58) Field of Classification Search ............ 514/44, 514/54, 210.02, 253.1, 274
See application file for complete search history.

(56) References Cited

U.S. PATENT DOCUMENTS

| | | | |
|---|---|---|---|
| 5,304,687 A | | 4/1994 | Bargiotti et al. |
| 5,605,703 A | | 2/1997 | Lambiez et al. |
| 5,861,406 A | * | 1/1999 | Wehrmann .................. 514/274 |
| 6,150,407 A | * | 11/2000 | Tuse et al. .................. 514/532 |
| 6,210,930 B1 | | 4/2001 | Filippini et al. |
| 6,239,137 B1 | * | 5/2001 | Karmali et al. ............. 514/274 |
| 6,284,737 B1 | | 9/2001 | Farquhar et al. |
| 6,653,455 B1 | | 11/2003 | Johdo et al. |
| 2005/0101563 A1 | * | 5/2005 | Pulaski et al. .................. 514/54 |
| 2006/0116404 A1 | | 6/2006 | Robinson et al. ............ 514/359 |

FOREIGN PATENT DOCUMENTS

WO    WO/95/08327    3/1995

OTHER PUBLICATIONS

Hoffmann et al., "Caboxyamido-Triazole modulates retinal pigment epithelial and choroidal endothelial cell attachment, migration, proliferation, and mmp-2 secretion of choroidal endothelial cells." Current Eye Research 2005:30;103-113.*

Franklin et al., "CAI is a Potent Inhibitor of Neovascularization and Imparts Neuroprotection in a Mouse Model of Ischemic Retinopathy." Investigative Ophthalmology & Visual Science 2004:45(10);3756-3766.*

Yasukawa et al., "Targeted Delivery of Anti-Angiogenic Agent TNP-470 Using Water-Soluble Polymer in the Treatment of Choroidal Neovascularization." IOVS 1999:40(11);2690-2696.*

Stanton et al., "Current methods for assaying angiogenesis in vitro and in vivo." Int. J. Exp. Path 2004:85;233-248.*

* cited by examiner

*Primary Examiner*—Frederick Krass
*Assistant Examiner*—Walter E Webb
(74) *Attorney, Agent, or Firm*—Rashida A. Karmali

(57) ABSTRACT

Method and composition of Carboxyamidotriazole orotate for treating age-related macular degeneration and other angiogenesis-dependent diseases.

1 Claim, 1 Drawing Sheet

USE OF CARBOXIAMIDOTRIAZOLE (CAI) OROTATE IN MACULAR DEGENERATION

1. FIELD OF INVENTION

Figure 1:
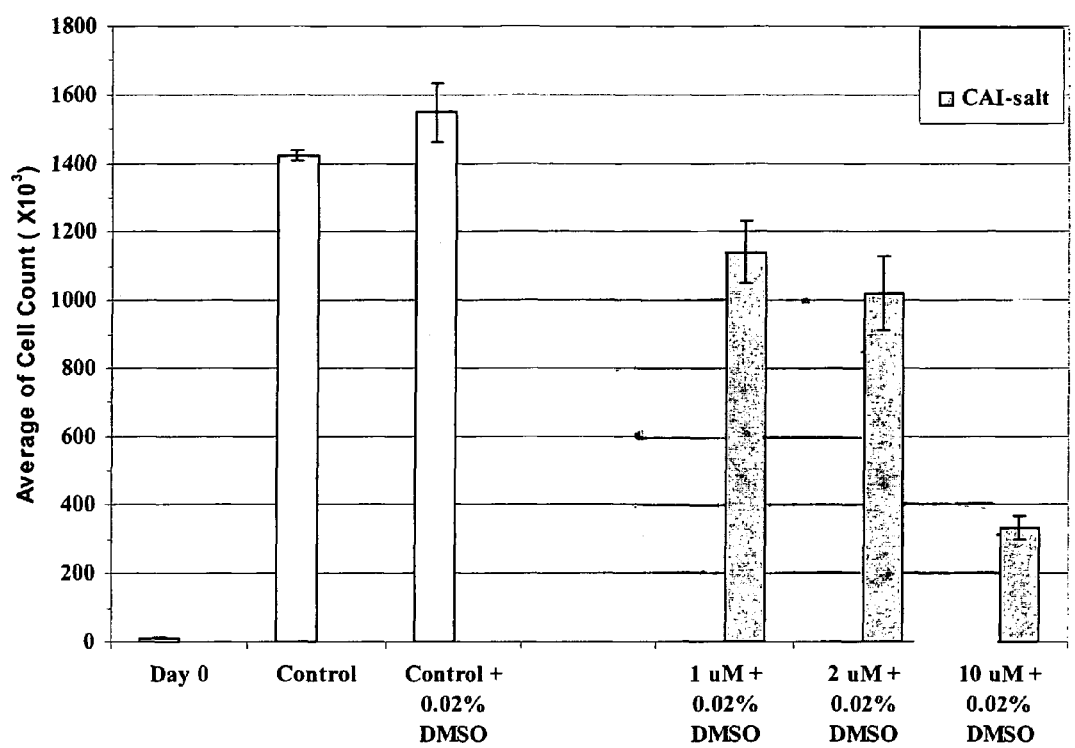

The present invention is directed to the treatment of age-related macular degeneration by the administration of an inhibitor of angiogenesis, Carboxyamidotriazole or 5 amino 1,2,3-triazole orotate (CAI Orotate). The invention relates to pharmaceutical compositions and methods for treating angiogenesis-dependent diseases.

2. BACKGROUND TO THE INVENTION

Age-related macular degeneration the leading cause of blindness among persons over fifty in the United States and in other countries. Two forms of age-relayed macular degeneration are known: 1) neovascular, also known as exudative age-related macular degeneration, and 2) nonneovascular, known as nonexudativeage-related macular degeneration. The neovascular macular degeneration involves angiogenesis. As used herein, the term "angiogenesis" means the generation of new blood vessels into a tissue or organ. Under normal physiological conditions, humans or animals only undergo angiogenesis in very specific situations such as in wound healing, fetal and embryonal development and formation of the corpus luteum, endometrium and placenta. The control of angiogenesis is a highly regulated system of angiogenic stimulators and inhibitors. The control of angiogenesis has been found to be altered in certain disease states and, in many cases, the pathological damage associated with the disease is related to the uncontrolled angiogenesis.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In advanced age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogenic-related factors contributes to the destruction of the joint. At a later stage, the angiogenic factors would promote new bone formation. Therapeutic intervention that prevents the bone destruction could halt the progress of the disease and provide relief for persons suffering with arthritis.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

Thus, new methods and compositions are needed that are capable of inhibiting angiogenesis and treating angiogenesis-dependent diseases.

Carboxyamidotriazole or 5 amino 1,2,3-triazole orotate (CAI Orotate) is currently under development for clinical use as an antitumor agent based on its antiangiogenic, antiproliferative and antimetastatic effects Kohn et al Cancer Res 52: 3208-3212, (1992); Bauer et al J. Pharm Exp Ther 292: 31-37 (2000) and Purow et al, Cancer Investigation 22: 577-587, (2004). U.S. Pat. No. 5,861,406 issued on Jan. 19, 1999 and U.S. Pat. No. 5,912,346 issued on Jul. 15, 1999, describe treatment and prevention of neoplasms with salts of aminoimizazole carboxamide and CAI triazole. Specifically, an orotate salt of CAI compared with CAI, was found to have improved antitumor effect in the Dunning rat model for prostate cancer. The mechanism of action for the enhancement in antitumor activity of CAI orotate was not described but was suggested to involve an alteration in cyclic nucleotide activity in the liver.

3. SUMMARY OF THE INVENTION

The present invention relates to the angiogenesis inhibitor, Carboxyamidotriazole or 5 amino 1,2,3-triazole orotate (CAI Orotate) and method for its use. In particular, therapy with the inhibitor exhibits strong anti-macular degeneration activity.

The present invention provides methods and compositions for treating diseases and processes mediated by undesired and uncontrolled angiogenesis by administering to a human or animal with the undesired angiogenesis a composition comprising Carboxyamidotriazole or 5 amino 1,2,3-triazole orotate (CAI Orotate), in a dosage sufficient to inhibit angiogenesis. The present invention is particularly useful for treating or for repressing macular degeneration.

4. BRIEF DESCRIPTION OF FIGURES

FIG. 1 illustrates the results of the proliferation assay for endothelial cells (HUVEC).

5. DETAILED DESCRIPTION OF THE INVENTION

The present invention relates to Carboxyamidotriazole or 5 amino 1,2,3-triazole orotate (CAI Orotate) and its the ability to inhibit endothelial proliferation when added to proliferating endothelial cells in vitro. CAI Orotate of the invention is useful for treating angiogenesis-related diseases, particularly macular degeneration, and angiogenesis-dependent diseases.

Angiogenesis-related diseases may be diagnosed and treated using the endothelial cell proliferation inhibiting compounds of the present invention. Angiogenesis-related diseases include, but are not limited to, ocular angiogenic diseases, for example, diabetic retinopathy, retinopathy of prematurity, macular degeneration, corneal graft rejection, neovascular glaucoma, retrolental fibroplasia, rubeosis; angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; Osler-Webber Syndrome; myocardial angiogenesis; plaque neovascularization; telangiectasia; hemophiliac joints; angiofibroma; and wound granulation. The endothelial cell proliferation inhibiting proteins of the present invention are useful in the treatment of disease of excessive or abnormal stimulation of endothelial cells. These diseases include, but are not limited to, intestinal adhesions, atherosclerosis, scleroderma, and hypertrophic scars, i.e., keloids. They are also useful in the treatment of diseases that have angiogenesis as a pathologic consequence such as cat scratch disease (Rochele minalia quintosa) and ulcers (Helobacter pylori).

6. EXAMPLES

Example 1

The Carboxyamidotriazole or 5 amino 1,2,3-triazole orotate (CAI Orotate) salt was prepared using the procedure described in U.S. Pat. No. 5,861,406. The molecular weight of CAI orotate is 581.

Example 2

Inhibition of Angiogenesis with Carboxyamidotriazole Orotate

Human umbilical vein endothelial cells (HUVEC) were treated with three different concentrations of Carboxyamidotriazole or 5 amino 1,2,3-triazole orotate (CAI Orotate) for 3 days. The cell number of each culture under different treatment conditions was counted. The assays were done in triplicate and the data are expressed as mean+/−standard deviation. Carboxyamidotriazole or 5 amino 1,2,3-triazole orotate (CAI Orotate) inhibited angiogenesis in a dose related manner (FIG. 1)

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Those skilled in the art will recognize, or be able to ascertain using no more than routine experimentation, any equivalents to the specific embodiments of the invention described herein. Such equivalents are intended to be encompassed by the claims.

What is claimed is:

1. A method of treating neovascular macular degeneration in an individual in need thereof, comprising administering orally or topically, to said individual, an amount of 5 amino 1,2,3-carboxyamidotriazole orotate effective to inhibit said neovascular macular degeneration.

* * * * *